(12) United States Patent
Kuentz et al.

(10) Patent No.: US 6,719,996 B2
(45) Date of Patent: Apr. 13, 2004

(54) GALENIC COMPOSITION FOR LOW BIOAVAILABILITY MEDICAMENTS

(75) Inventors: Martin Kuentz, Muttenz (CH); Dieter Roethlisberger, Muttenz (CH)

(73) Assignee: Hoffmann-La Roche Inc., Nutley, NJ (US)

(*) Notice: Subject to any disclaimer, the term of this patent is extended or adjusted under 35 U.S.C. 154(b) by 78 days.

(21) Appl. No.: 10/015,925

(22) Filed: Dec. 10, 2001

(65) Prior Publication Data

US 2002/0114837 A1 Aug. 22, 2002

(30) Foreign Application Priority Data

Dec. 14, 2000 (EP) .............................. 00127414

(51) Int. Cl.⁷ .............................. A61K 9/28; A61K 9/68

(52) U.S. Cl. ........................ 424/441; 424/439; 424/484; 424/485

(58) Field of Search ................. 424/484, 485, 424/451, 464, 439, 441

(56) References Cited

U.S. PATENT DOCUMENTS 6,375,982 B1 * 4/2002 Cherukuri .................. 424/484

FOREIGN PATENT DOCUMENTS

EP 1 035 115 9/2000
WO WO 97/36577 10/1997

OTHER PUBLICATIONS

Aungst B J, et al., *International Journal of Pharmaceutics, Amsterdam, NL,* vol. 156, No. 1, pp. 79–88 (1997).
Serajuddin, et al., *Journal of Pharmaceutical Sciences, American Pharmaceutical Association, Washington, US,* vol. 88, No. 10, pp. 1058–1066 (1999).

* cited by examiner

*Primary Examiner*—Thurman K. Page
*Assistant Examiner*—Liliana Di Nola-Baron
(74) *Attorney, Agent, or Firm*—George W. Johnston; Patricia S. Rocha-Tramaloni; Kimberly J. Prior

(57) ABSTRACT

A pharmaceutical composition for oral administration of an active compound having a bioavailability of 20% or less. The composition comprises, based on its total weight, from 0.01% to about 15% (w/w) of said active compound molecularly dissolved in the composition, from 30 to 80% (w/w) of an edible lipid matrix and from 1 to 20% (w/w) of an edible emulsifier, the ratio between the dose weight of the active compound and its solubility in the composition being equal to or greater than 0.6 ml. The high percentage of fat (30–80%) enables a considerable increase the amount of the drug that is molecularly dispersed in the dosage form, thus allowing a significant reduction in the number of unit doses that must be taken daily-by patients.

27 Claims, No Drawings

GALENIC COMPOSITION FOR LOW BIOAVAILABILITY MEDICAMENTS

BACKGROUND OF THE INVENTION

1. Field

The present invention relates to novel galenic compositions and, in particular, to compositions for oral administration of medicaments.

2. Description

Oral dosage forms are designed to enable sufficient availability of the active compound at its site of action. The bioavailability of a drug depends on several parameters, such as the physicochemical nature of the active compound, the dosage form, as well as physiological factors.

Many substances obtained from modern drug discovery are problematic because of insufficient bioavailability. Such molecules often exhibit very low aqueous solubility and limited solubility in oils. Thus, a problem arises if high drug loads must be obtained. This is often the case with compositions in soft or hard gelatin capsules, wherein not only is the solubility of the drug in the medium very low, but the filling volume of the capsules is limited.

To enhance bioavailability of orally administered drugs, Self-Emulsifying Drug Delivery Systems (SEDDS) may be used. SEDDS are mixtures of oils and surfactants, ideally isotropic (sometimes including cosolvents), which emulsify under conditions of gentle agitation, similar to those which would be encountered in the gastrointestinal tract. When such a composition is released into the lumen of the gut, it disperses to form a fine emulsion, so that the drug remains in solution in the gut, avoiding the dissolution step that frequently limits the rate of absorption of hydrophobic drugs from the crystalline state. The use of SEDDS usually leads to improved bioavailability and/or a more consistent temporal profile of absorption from the gut. A description of compositions of SEDDS can be found for instance in C. W. Pouton, *Advanced Drug Delivery Reviews*, 25: 47–58 (1997).

While SEEDS increase bioavailability, solubility of the drugs in such systems may not be increased considerably . Additionally, SEDDS compositions are usually administered by means of capsules, whose volume cannot be arbitrarily increased without negatively affecting the patient's compliance. Accordingly, for elevated daily therapeutic amounts, a patient must swallow several capsules to provide his body with the necessary amount of drug.

The problem solved by the present invention is how to provide a galenic composition for oral administration of medicaments that show low bioavailability and poor solubility in polar and/or apolar media.

SUMMARY OF THE INVENTION

The subject invention provides a pharmaceutical composition for orally administering an active compound having a bioavailability of 20% or less. The composition comprises, based on the total weight of the composition, from about 0.01% to about 15% (w/w) of an active compound molecularly dissolved in the composition, from about 30% to about 80% (w/w) of an edible lipid matrix, and from about 1% to about 20% (w/w) of an edible emulsifier, the ratio between the dose weight of the active compound and its solubility in the composition being equal to or greater than 0.6 ml.

Preferably, the edible lipid matrix is present in a concentration of from about 50% to about 75% (w/w) of the total weight of the composition. Preferred concentrations emulsifier are from about 1% to about 10% (w/w) of the total weight of the composition and more preferably from about 2% to about 8% (w/w) of the total weight of the composition.

The lipid matrix is favorably selected from the group consisting of natural vegetable triglycerides, semi-synthetic vegetable triglycerides, and hydrogenated vegetable glycerides, for cocoa butter.

The emulsifier is favorably selected from the group consisting of lecithins and polyglycolized triglycerides, such as soya lecithin. Sweeteners and/or flavors may be added.

The ratio between the dose weight of the active compound and its solubility in the composition is favorably equal to or greater than 1.2 ml, more favorably between about 1.2 ml and about 10 ml, and most favorably between about 3 ml and about 7 ml.

Favored active compounds are selected from the group consisting of sulfonamides, dihydropiridines, isoquinoline derivatives, 4-phenylpyridin derivatives, and phenylamino-[5-ethoxy-2-fluoro-4-(2-hydroxy-ethoxy)-phenyl] derivatives. 4-Phenylpyridin derivatives are favored. Another favored group of active compounds are selected from the group consisting of 2-(3,5-bis-trifluoromethyl-phenyl)-N-methyl-N-(6-morpholin-4-yl-4-o-tolyl-pyridin-3-yl)-isobutyramide; 2-(3,5-bis-trifluoromethyl-phenyl)-N-methyl-N-[6-(4-methyl-piperazin-1-yl)-4-o-tolyl-pyridin-3-yl]-isobutyramide; and 2-(3,5-bis-trifluoromethyl-phenyl)-N-[4-(2-chloro-phenyl)-pyridin-3-yl]-N-methyl-isobutyramide.

Another aspect of the subject invention is a process for preparing a pharmaceutical composition. This process comprises (i) selecting an active compound showing a bioavailability of 20% or less, an edible lipid matrix, and an edible emulsifier; and (ii) mixing, based on the total weight of the composition, from about 0.01% to about 15% (w/w) of an active compound showing a bioavailability of 20% or less, from about 30% to 80% (w/w) of an edible lipid matrix, and from 1% to about 20% (w/w) of an edible emulsifier, so that the ratio between the dose weight of the active compound and its solubility in the composition is equal to or greater than 0.6 ml.

DETAILED DESCRIPTION OF THE PREFERRED EMBODIMENTS

The subject invention will now be discussed in terms of its preferred embodiments. These embodiments are set forth to aid in understanding the invention but are not limiting.

According to the present invention, the problem of providing a galenic composition for oral administration of medicaments which show low bioavailability and poor solubility in polar and/or apolar media is solved by providing a pharmaceutical composition for oral administration of an active compound showing a bioavailability of twenty percent (20%) or less, characterized in that it comprises, based on the total weight of the composition, from 0.01% to about 15% (w/w) of said active compound molecularly dissolved in the composition, from 30 to 80% (w/w) of an edible lipid matrix and from 1 to 20% (w/w) of an edible emulsifier, the ratio between the dose weight (mg) of the active compound and its solubility (mg/ml) in the composition being equal to or greater than 0.6 ml.

The definition of the bioavailability is given in the examples and the above value of 20% or less is determined on the basis of a simple oral formulation (e.g. a hard gelatin capsule) without additional exipients and wherein the active compound is in the crystalline form. The dissolution of solid pharmaceutical active compounds in polar and apolar media is dealt for instance in A. Martin, *Physical Pharmacy*. 4th ed., Lea Febiger London, (1993), 221–237. The composition according to the present invention can be defined as Self-Emulsifying Lipid Matrix (SELM) since, as the SEEDS compositions, it emulsifies at 37° C. under condition of gentle agitation. The high percentage of fat (30–80%)

enables to considerably increase the amount of drug molecularly dispersed in the dosage form. SELM formulations are applicable in the cases where the volume available for the molecular dispersion of the drug must be equal to or greater than 0.6 ml. The volume available for the molecular dispersion of the drug is defined as ratio between the dose weight of the active compound in the single dose (mg) and its solubility (mg/ml) in the composition.

Use of the subject compositions allows for a significant reduction in the number of unit doses that must be taken daily by patients, thus increasing the overall acceptance of a given medicament. It has been demonstrated, in particular in the case of children and elderly people, that the positive result of a therapy depends on patient compliance which can be negatively impacted by a complex program of administration.

The relative high amount of emulsifier in the present composition imbues a self-emulsifying character which considerably increases the bioavailability of the active compound in the body.

Pharmaceutical compositions according to the present invention can be administered in form of chewing tablets having a visual aspect similar to that of chocolate bars of different forms and sizes, or that of normal chocolates (pralines).

This enables to have a single dose volume, and therefore a drug load, which is sensibly higher than those of conventional SEEDS compositions which, on their turn, have to be administered by swallowing capsules.

Preferably, the composition of the invention has a visual aspect similar to that of normal chocolates (pralines).

According to a preferred embodiment, the ratio between the dose weight of the active compound and its solubility in the composition is equal to or greater than 1.2 ml, more preferably it varies between 0.6 and 10 ml and, still more preferably, between 3 and 7 ml. According to a further preferred embodiment of the present invention, the edible lipid matrix is present in a concentration varying from 50 to 75% (w/w) of the total weight of the composition, and can be chosen among the natural and semi-synthetic vegetable triglycerides, such as coconut butter and cocoa butter, and hard fat (hydrogenated vegetable glycerides) respectively. Most preferably, cocoa butter is used as lipid matrix.

The edible emulsifier is preferably chosen among those that do not show substantial side effects. Advantageously, it is present in a concentration varying from 1 to 10% (w/w) and, still more advantageously, in a concentration varying from 2 to 8% (w/w) of the total weight of the composition. It is preferably selected from the group consisting of lecithins, such as natural lecithin, synthetic lecithin, soya lecithin, egg lecithin, synthetic dipalmitinlecithin, partially or fully hydrogenated lecithin and mixtures thereof, polyglycolized triglycerides, such as Cremophor EL and Cremophor RH and polyethylenglycol sorbitane fatty esters, such as Polysorbate 20, 40, 65, 80 and 85.

Most preferably lecithin, and in particular soya lecithin, is used as emulsifier in the present compositions.

To obtain a better acceptance, the composition according to the present invention may contain further additives in usual concentrations. These include sweeteners, such as sucrose and aspartame, as well as flavors such as vanillin, honey and nut flavor.

As stated above, the present invention is suitable for the oral administration of active compounds which show a low bioavailability. Active compounds having a bioavailability of 20% or less, preferably of 10% or less, can be suitably administered by means of the composition according to the present invention. Examples of these active compounds can be found among the sulfonamides, dihydropiridines, iso- quinoline derivatives, 4-phenylpyridin derivatives and phenylamino-[5-ethoxy-2-fluoro-4-(2-hydroxy-ethoxy)-phenyl] derivatives. According to a preferred embodiment, the present composition is used for active compounds selected among the group of the 4-phenylpyridin derivatives such as 2-(3,5-bis-trifluoromethyl-phenyl)-N-methyl-N-(6-morpholin-4-yl-4-o-tolyl-pyridin-3-yl)-isobutyramide;

2-(3,5-bis-trifluoromethyl-phenyl)-N-methyl-N-[6-(4-methyl-piperazin-1-yl)-4-o-tolyl-pyridin-3-yl]-isobutyramide; and 2-(3,5-bis-trifluoromethyl-phenyl)-N-[4-(2-chloro-phenyl)-pyridin-3-yl]-N-methyl-isobutyramide.

The above three compounds, whose synthesis maybe found in EP-A-1035115, are characterized by valuable therapeutic properties. They are highly selective antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue. The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (*Neurosci. Res.*, 7:187–214 (1996), anxiety (*Can. J. Phys.*, 75: 612–621 (1997) and depression (*Science*, 281:1640–1645 (1998).

Evidence for the usefulness of tachykinin receptor antagonists in pain, headache, especially migraine, Alzheimer's disease, multiple sclerosis, attenuation of morphine withdrawal, cardiovascular changes, edema, such as edema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases has been reviewed in "Tachykinin Receptor and Tachykinin Receptor Antagonists", *J. Auton. Pharmacol.*, 13: 23–93 (1993).

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for treating motion sickness and induced vomiting.

In addition, the reduction of cisplatin-induced emesis by a selective neurokinin-1-receptor antagonist has been described in *The New England Journal of Medicine*, 340(3):190–195 (1999).

The usefulness of neurokinin 1 receptor antagonists for treating certain forms of urinary incontinence is further described in *Neuropeptides*, 32(1):1–49 (1998) and *Eur. J. Pharmacol.*, 383(3):297–303 (1999).

An object of the present invention is also to provide a process for preparing a pharmaceutical composition as described above, which process comprises mixing, based on the total weight of the composition, from 0.01% to about 15% (w/w) of an active compound showing a bioavailability of 20% or less, from 30 to 80% (w/w) of an edible lipid matrix and from 1 to 20% (w/w) of an edible emulsifier, the ratio between the dose weight of the active compound and its solubility in the composition being equal to or greater than 0.6 ml. Preferably the entire manufacture process is carried out in a conventional industrial mixer with a build-in homogenizer. The dosing is preferably done with molds or by direct filling of suitably designed blisters.

The invention will be now illustrated in details by the following examples. Examples 1–4 relate to four compositions according to the present invention, while comparative Example 5 is directed to a SEEDS composition.

The solubility of 2-(3,5-bis-trifluoromethyl-phenyl)-N-methyl-N-(6-morpholin-4-yl-4-o-tolyl-pyridin-3-yl)-isobutyramide in cocoa butter/lecithin mixtures has been measured and found to be less than 15 mg/ml.

Preparation of the Compositions

EXAMPLE 1

8 g Cremophor RH 40 were dispersed in 70.08 g of cocoa butter, previously warmed to 70–80° C. The temperature of the resulting mixture was then reduced to about 50–60° C. and 1.4 g of 2-(3,5-bis-trifluoromethyl-phenyl)-N-methyl-N-(6-morpholin-4-yl-4-o-tolyl-pyridin-3-yl)-isobutyramide were dissolved together with 0.02 g vanillin. The temperature of the resulting mixture was further reduced to 40° C. and 0.5 g aspartame were added. Finally, 20 g of milk powder were added at about 35° C. (upper limit of the melting interval of cocoa butter). The resulting homogeneous mixture was then dosed in moulds whereby SELM tablets of 5 g each (corresponding to a volume of about 5 ml), and showing a ratio between the dose weight of the active compound and its solubility in the composition of at least 4.67 ml, were obtained.

EXAMPLE 2

The procedure of Example 1 was repeated with the following composition:

1.4 g 2-(3,5-Bis-trifluoromethyl-phenyl)-N-methyl-N-(6-morpholin-4-yl-4-o-tolyl-pyridin-3-yl)-isobutyramide
70.08 g Cocoa butter
8.0 g Lipoid S 100
20.0 g Whole milk powder
0.5 g Aspartame
0.02 g Vanillin

EXAMPLE 3

The procedure of Example 1 was repeated with the following composition:

1.4 g 2-(3,5-Bis-trifluoromethyl-phenyl)-N-methyl-N-(6-morpholin-4-yl-4-o-tolyl-pyridin-3-yl)-isobutyramide
77.08 g Cocoa butter
1.0 g Cremophor RH 40
20.0 g Whole milk powder
0.5 g Aspartame
0.02 g Vanillin

EXAMPLE 4

The procedure of Example 1 was repeated with the following composition:

1.4 g 2-(3,5-Bis-trifluoromethyl-phenyl)-N-methyl-N-(6-morpholin-4-yl-4-o-tolyl-pyridin-3-yl)-isobutyramide
74.08 g Cocoa butter
4.0 g Lipoid S 40
20.0 g Skimmed milk powder
0.5 g Aspartame
0.02 g Vanillin

EXAMPLE 5 (Comparative SEEDS Composition)

0.21 g 2-(3,5-Bis-trifluoromethyl-phenyl)-N-methyl-N-(6-morpholin-4-yl-4-o-tolyl-pyridin-3-yl)-isobutyramide were weighted in a 20 ml glass vial. 11.79 g of SEDDS (obtained by mixing 4.95 g Tween 80 and 6.84 g Miglyol 812 under vigorous stirring and at 70° C.) were added thereto and the active compound was brought into solution, always under stirring and at 70° C. A yellow clear solution was obtained as final product.

Test of Oral Bioavailability in Dogs

Oral bioavailability tests were performed with beagle dogs. Each composition was orally administered to the different beagle dogs typically at a dose of 6 mg/kg body weigh. Blood samples were collected during 48 h and the drug concentration was determined using a HPLC method. The blood concentrations after oral and intravenous administration were plotted against time and the areas under the curve for the per oral ($AUC_{p.o.}$) and intravenous ($AUC_{i.v.}$) drug administration were calculated individually and using the trapezoidal rule. The bioavailability (%) was obtained from the dose normalized $AUC_{oral}$ divided by the dose normalized $AUC_{i.v.}$.

As shown in Table 1, the compositions according to the present invention showed excellent bioavailabilities up to 68%, as well as excellent drug loads of 70 mg per unit dose. Table 2 shows that classical solid compositions did not enable sufficient bioavailability of the drug 2-(3,5-bis-trifluoromethyl-phenyl)-N-methyl-N-(6-morpholin-4-yl-4-o-tolyl-pyridin-3-yl)-isobutyramide. The use of SEEDS compositions enabled an increase of the bioavailability of 2-(3,5-bis-trifluoromethyl-phenyl)-N-methyl-N-(6-morpholin-4-yl-4-o-tolyl-pyridin-3-yl)-isobutyramide up to 27%. However the limitation of the capsule volume did not allow to dissolve more than 20 mg of 2-(3,5-bis-trifluoromethyl-phenyl)-N-methyl-N-(6-morpholin-4-yl-4-o-tolyl-pyridin-3-yl)-isobutyramide per hard gelatin capsule (standard size 00).

TABLE 1

Bioavailability of 2-(3,5-bis-trifluoromethyl-phenyl)-N-methyl-N-(6-morpholin-4-yl-4-o-tolyl-pyridin-3-yl)-isobutyramide from the new drug delivery system (SELM)

| Ex | Drug load [mg/unit dose] | Bioavailabiity (%) of fasted dogs | | Bioavailabiity (%) of fed dogs | |
|---|---|---|---|---|---|
| | | first dog | second dog | first dog | second dog |
| 1 | 70 | 7* | 4* | 17 | 22 |
| 2 | 70 | 22 | 30 | 53 | 42 |
| 3 | 70 | 19 | — | 39 | 21 |
| 4 | 70 | 45 | 47 | 46 | 68** |

*calculated from AUC (0–8 h)
**best result obtained

TABLE 2

Bioavailability of 2-(3,5-bis-trifluoromethyl-phenyl)-N-methyl-N-(6-morpholin-4-yl-4-o-tolyl-pyridin-3-yl)-isobutyramide from compositions with crystalline drug and SEDDS

|  | Bioavailability (%) of first dog (fasted) | Bioavailabiity (%) of second dog (fasted) |
| --- | --- | --- |
| HCl Salt in Capsule | 1.7 | 1.1 |
| Hydrogen sulfate in Capsule | 2.7 | 3.1 |
| Milled Base in a Suspension filled in Capsule | 1.2 | 0.6 |
| Microsuspension filled in Capsules | 7 | 1.2 |
| SEDDS (Miglyol 812/Tween 80) (Example 5) | 13 | 27 |

The compositions according to the present invention enable a considerable increase in the drug load of active compounds that are hardly soluble in water and/or oil. Since it can be administered in form of chewing tablets, the present compositions may have elevated single dose volumes. This enables to further improve the drug load and, simultaneously, to reduce the number of unit doses to be taken daily.

Furthermore, the relative high amount of emulsifier confers to the present composition a self-emulsifying character that enables a considerable increase the bioavailability of the active compound in the body.

Upon reading the present specification various alternative embodiments will become obvious to the skilled artisan. These variations are to be considered within the scope and spirit of the subject application, which is only to be limited by the claims that follow and their equivalents.

What is claimed is:

1. A pharmaceutical composition for orally administering an active compound having a bioavailability of 20% or less, which comprises, based on the total weight of the composition, from about 0.01% to about 15% (w/w) of an active compound molecularly dissolved in the composition, from about 30% to about 80% (w/w) of an edible lipid matrix, and from about 1% to about 20% (w/w) of an edible emulsifier, the ratio between the dose weight of the active compound and its solubility in the composition being equal to or greater than 0.6 ml and which comprises a chewable unit dosage form resembling a piece of chocolate.

2. The pharmaceutical composition according to claim 1, wherein the edible lipid matrix is present in a concentration of from about 50% to about 75% (w/w) of the total weight of the composition.

3. The pharmaceutical composition according to claim 1, wherein the emulsifier is present in a concentration of from about 1% to about 10% (w/w) of the total weight of the composition.

4. The pharmaceutical composition according to claim 3, wherein the emulsifier is present in a concentration of from about 2% to about 8% (w/w) of the total weight of the composition.

5. The pharmaceutical composition according to claim 1, wherein the lipid matrix is selected from the group consisting of natural vegetable triglycerides, semi-synthetic vegetable triglycerides, and hydrogenated vegetable glycerides.

6. The pharmaceutical composition according to claim 5, wherein the lipid matrix is cocoa butter.

7. The pharmaceutical composition according to claim 1, wherein the emulsifier is selected from the group consisting of lecithins and polyglycolized triglycerides.

8. The pharmaceutical composition according to claim 7, wherein the emulsifier is soya lecithin.

9. The pharmaceutical composition according to claim 1 further comprising sweeteners or flavors.

10. The pharmaceutical composition according to claim 1, wherein the ratio between the dose weight of the active compound and its solubility in the composition is equal to or greater than 1.2 ml.

11. The pharmaceutical composition according to claim 10, wherein the ratio between the dose weight of the active compound and its solubility in the composition is between about 1.2 ml and about 10 ml.

12. The pharmaceutical composition according to claim 11, wherein the ratio between the dose weight of the active compound and its solubility in the composition is between about 3 ml and about 7 ml.

13. The pharmaceutical composition according to claim 1, wherein the active compound is selected from the group consisting of sulfonamides, dihydropiridines, isoquinoline derivatives, 4-phenylpyridin derivatives, and phenylamino-[5-ethoxy-2-fluoro-4-(2-hydroxy-ethoxy)-phenyl] derivatives.

14. The pharmaceutical composition according to claim 13, wherein the active compound is a 4-phenylpyridin derivative.

15. The pharmaceutical composition according to claim 14, wherein the active compound is selected from the group consisting of 2-(3,5-bis-trifluoromethyl-phenyl)-N-methyl-N-(6-morpholin-4-yl-4-o-tolyl-pyridin-3-yl)-isobutyramide; 2-(3,5-bis-trifluoromethyl-phenyl)-N-methyl-N-[6-(4-methyl-piperazin-1-yl)-4-o-tolyl-pyridin-3-yl]-isobutyramide; and 2-(3,5-bis-trifluoromethyl-phenyl)-N-[4-(2-chloro-phenyl)-pyridin-3-yl]-N-methyl-isobutyramide.

16. The pharmaceutical composition according to claim 15, wherein the edible lipid matrix is present in a concentration of from about 50% to about 75% (w/w) of the total weight of the composition.

17. The pharmaceutical composition according to claim 16, wherein the emulsifier is present in a concentration of from about 1% to about 10% (w/w) of the total weight of the composition.

18. The pharmaceutical composition according to claim 17, wherein the emulsifier is present in a concentration of from about 2% to about 8% (w/w) of the total weight of the composition.

19. The pharmaceutical composition according to claim 15, wherein the lipid matrix is selected from the group consisting of natural vegetable triglycerides, semi-synthetic vegetable triglycerides, and hydrogenated vegetable glycerides.

20. The pharmaceutical composition according to claim 19, wherein the lipid matrix is cocoa butter.

21. The pharmaceutical composition according to claim 15, wherein the emulsifier is selected from the group consisting of lecithins and polyglycolized triglycerides.

22. The pharmaceutical composition according to claim 21, wherein the emulsifier is soya lecithin.

23. The pharmaceutical composition according to claim 15 further comprising sweeteners or flavors.

24. The pharmaceutical composition according to claim 15, wherein the ratio between the dose weight of the active compound and its solubility in the composition is equal to or greater than 1.2 ml.

25. The pharmaceutical composition according to claim 24, wherein the ratio between the dose weight of the active compound and its solubility in the composition is between about 1.2 ml and about 10 ml.

26. The pharmaceutical composition according to claim 25, wherein the ratio between the dose weight of the active compound and its solubility in the composition is between about 3 ml and about 7 ml.

27. A process for preparing a pharmaceutical composition comprising a chewable unit dosage form resembling a piece of chocolate, which process comprises:

(i) selecting an active compound showing a bioavailability of 20% or less, an edible lipid matrix, and an edible emulsifier; and (ii) mixing, based on the total weight of the composition, from about 0.01% to about 15% (w/w) of an active compound showing a bioavailability of 20% or less, from about 30% to about 80% (w/w) of an edible lipid matrix, and from 1% to about 20%(w/w) of an edible emulsifier, so that the ratio between the dose weight of the active compound and its solubility in the composition is equal to or greater than 0.6 ml.

* * * * *